United States Patent [19]
Johnston

[11] 4,335,719
[45] Jun. 22, 1982

[54] IRRIGATION DEVICE

[76] Inventor: Samuel R. Johnston, 41 Laurel Hill Rd., Lisburn, County Antrim, Ireland

[21] Appl. No.: 231,200

[22] Filed: Feb. 4, 1981

[51] Int. Cl.³ .............................................. A61M 3/00
[52] U.S. Cl. ................................. 128/246; 128/349 B
[58] Field of Search ............... 128/246, 245, 240, 241, 128/227, 224, 349 R, 349 B, 349 BV, 350 R, 350 V

[56] References Cited

U.S. PATENT DOCUMENTS

| | | | |
|---|---|---|---|
| 1,847,954 | 3/1932 | Fisher | 128/227 |
| 1,937,362 | 11/1933 | Schellberg | 128/227 |
| 1,973,845 | 9/1934 | Chenoweth | 128/227 |
| 2,022,742 | 12/1935 | Salerni | 128/227 |

FOREIGN PATENT DOCUMENTS

| | | |
|---|---|---|
| 358436 | 3/1921 | Fed. Rep. of Germany . |
| 672779 | 3/1939 | Fed. Rep. of Germany . |
| 382099 | 9/1907 | France . |
| 399288 | 2/1909 | France . |
| 818952 | 10/1937 | France . |
| 108382 | 3/1924 | Switzerland . |

*Primary Examiner*—John D. Yasko
*Attorney, Agent, or Firm*—Lawrence Rosen

[57] ABSTRACT

In an irrigation device, irrigation fluid flows from a reservoir 12 via an inflow passage 11 to a bladder 22 and out through an outflow passage 15 to a collection bag 17. Debris such as blood clots which tend to form at inlet 23 is disturbed and removed by manipulation of the balloon 18 using a procedure of closing and opening clips at P, Q and R in sequence.

10 Claims, 4 Drawing Figures

IRRIGATION DEVICE

The invention relates to irrigation devices for use in the irrigation of body cavities.

Irrigation catheters are commonly used, especially following an operation, to irrigate body cavities in humans and animals. The invention is intended to be used with dual-flow catheters and has particular though not exclusive application in irrigating bladders. Considerable difficulties arise during early periods of post-operative care due to debris and especially blood clots gathering at the mouth of an evacuating passage and preventing further exit of irrigating fluid through the passage. At present when blockages occur it is necessary to connect some kind of separate pumping arrangement, for example a syringe, and flush out the debris. In most cases this requires considerable preparation as an aseptic procedure is required to avoid the risk of introducing infection to the body cavity.

Dual-flow catheters have an inlet passageway which passes along the length of the catheter from an inlet at the end of the catheter which, in use, is outside the body to an outlet at the tip of the catheter and an outlet passageway which passes along the length of the catheter from an inlet at the tip of the catheter to an outlet at the end of the catheter which in use, is outside the body.

To ensure that the catheter remains in the body cavity it is common for irrigation catheters to be fitted with an inflatable collar adjacent the tip of the catheter which is inflated after the catheter is inserted into the body cavity.

According to the present invention there is provided a device for use in the irrigation of a body cavity which comprises:

(a) a first passageway having a liquid inlet at one end thereof, which is connectible to a source of irrigation liquid and a liquid outlet at the other end thereof which is connected to or connectible to the inlet passageway of a dual flow catheter.

(b) a second passageway having a liquid inlet at one end thereof which is connected to or connectible to the outlet passageway of said dual flow catheter and a liquid outlet at the other end thereof, (c) an enlarged deformable portion of the second passageway located downstream of said one end of the second passageway, (d) first flow-controlling means downstream of the enlarged deformable portion to prevent or impede the flow of liquid through the second passageway the arrangement being such that when the flow-controlling means are operated to prevent or impede the flow of liquid through the second passageway and the enlarged deformable portion is manipulated to reduce its volume, the flow of liquid in the second passageway upstream of the enlarged deformable portion and in the outlet passageway of the dual flow catheter is reversed.

A by-pass-passageway and further flow-controlling means may be provided as hereinafter described. The irrigation devices of the present invention may be connected to a commercially available catheter or may be incorporated into a catheter assembly such that the first and second passageways communicate with the inlet and outlet passageways of the catheter.

Irrigation devices according to the invention will now be described by way of example with reference to the accompanying diagrammatic drawings in which.

Figure 1:
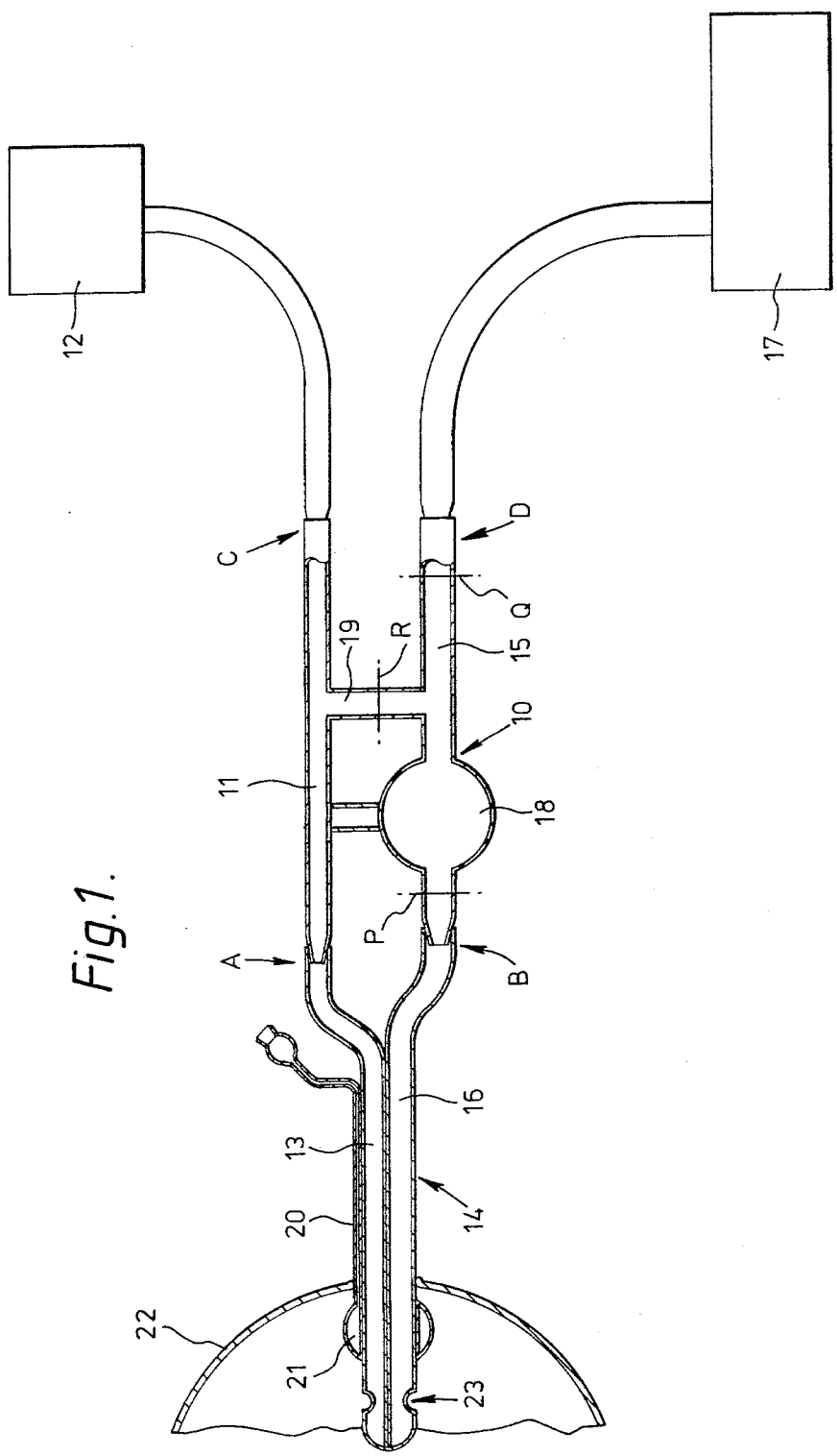
FIG. 1 shows one form of irrigation device for attachment to a dual flow catheter.

Referring to the drawings, in FIG. 1 an irrigation device 10 comprises an inflow passage 11 connected between an irrigation fluid reservoir 12 and the inlet 13 of a dual flow catheter 14. An outflow passage 15 is connected between the outlet 16 of the catheter 14 and a collection bag 17. An expanded squeezable balloon 18 is provided near the inlet of the outflow passage 15 and a by-pass 19 is provided between the inflow and outflow passages 11 and 15.

A channel 20 extends along the catheter 14 to an expandable annulus 21 which is used when inflated to secure the catheter 14 in a bladder 22, or other body cavity. The connections between the catheter arrangement and the catheter 14 at A and B and the connections between the catheter arrangement and the reservoir 12 and the bag 17 at C and D are made in an aseptic environment and need not be disturbed once the catheter 14 is in position. Three clips (not shown) are provided at P, Q and R for closing off or at least restricting flow when required in passages 15, at either side of the balloon 18, and by-pass 19, respectively.

In use, irrigation of the bladder 22 is carried out by flowing fluid from the reservoir 12 via the inflow passage 11 and catheter 14 to the bladder 22. Fluid leaves the bladder 22 and passes to the bag 17 via the outflow passage 15. The clip (not shown) at R is adjusted to maintain the bypass 19 closed and the clips (not shown) at P and Q are in their open position.

If a blockage occurs at an inlet 23 of the outlet 16 of the catheter 14, it can be cleared in one of three ways. For a minor blockage, or even as a routine procedure, flow in the outlet passage 15 can be restricted by closure of the clip at Q (or even by manually applied pressure to the outlet passage 15 or the tube connected to the bag 17) and then the balloon 18 squeezed. This causes a reverse flow in outlet 16 of catheter 14 to dislodge or disturb any debris formed at the inlet 23. The balloon is then released and the constriction just applied released to allow irrigation fluid to flow once more towards the bag 17.

For more severe blockages, which especially are likely to occur in an immediate post-operative period, more precise routines are normally required to relieve the blockage.

For clearing a severe blockage, firstly the clip at Q is closed and the balloon 18 is then squeezed to dislodge and break up debris obstructing the inlet 23. The balloon is then released and debris will be evacuated towards the balloon 18. The clip at Q is then opened and irrigation fluid restored allowing debris to pass to the bag 17.

For clearing a very severe blockage, firstly the clip at Q is closed, and the balloon is then squeezed to dislodge and break up debris obstructing the inlet 23. The balloon is then released to draw debris from the region of inlet 23 into the balloon 18. The clip at P is then closed, the clip at Q opened, and the balloon squeezed to expel debris towards the bag 17. The clip at Q is then closed and the clip at R opened to allow the balloon to fill with irrigating fluid directly from the reservoir 12. The clip at R is then closed and the clips P and Q opened to allow irrigation fluid to flow again into and out of bladder 22 in the normal manner. If debris is not cleared by this procedure, the balloon 18 can be squeezed again after being refilled with clear fluid from reservoir 12 and the procedure of dislodging and breaking up debris repeated as often as necessary until the debris is evacuated.

It will be noted that each debris clearing procedure for dislodging debris from the inlet 23 is carried out keeping the irrigation system closed, whether for a minor or severe blockage. The procedures are carried out conveniently, and as frequently as required, without risk of introducing infection and without aseptic techniques being required. The balloon 18 is preferably positioned as near as possible to the region at the inlet 23 where debris tends to form to cause a blockage to minimise dead-space therebetween.

Further, as the balloon 18 is re-filled by the irrigation fluid from the reservoir 12, no separate irrigation fluid supply need be provided.

The irrigation device may be formed of plastics material or other relatively cheap material and can therefore be provided as a disposable commodity.

Figure 2:
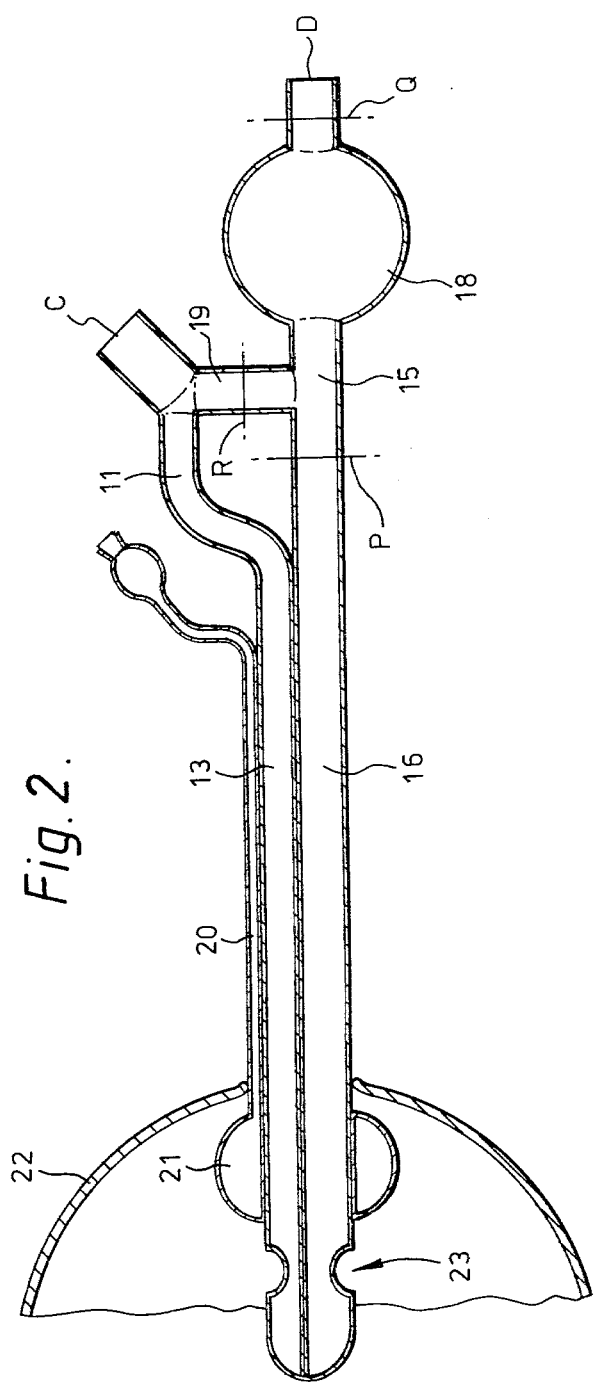
FIG. 2 shows another form of irrigation device formed as a unitary structure with a catheter.

In FIG. 2, the irrigation device 10 is arranged as a unitary construction together with the catheter 14 of FIG. 1, with similar parts like numbered. The operation and use of such a unitary construction is generally as already described with reference to FIG. 1.

Figure 3:
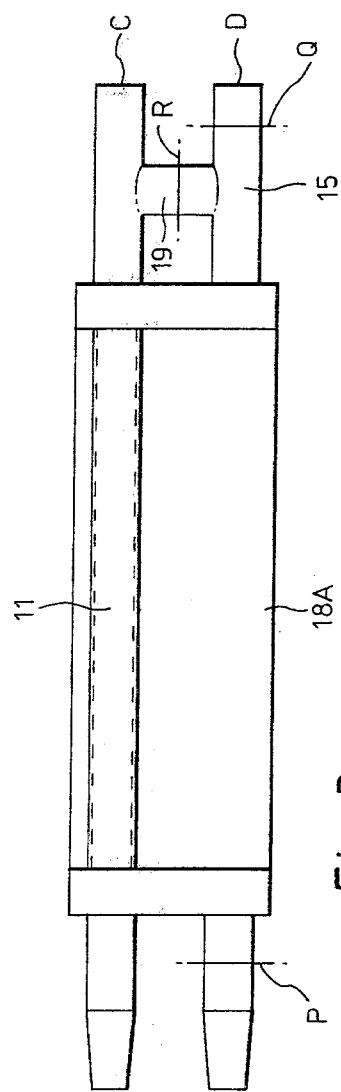
FIG. 3 shows another form of irrigation device.

In FIG. 3, the irrigation device 10 is similar to the irrigation device in FIG. 1. The balloon 18 of FIG. 1 is replaced by a cylindrical portion 18A of larger diameter than the outflow passage 15. The inflow passage 11 passes through the cylindrical portion 18A. The operational use and clearance of debris being generally as earlier described.

Figure 4:
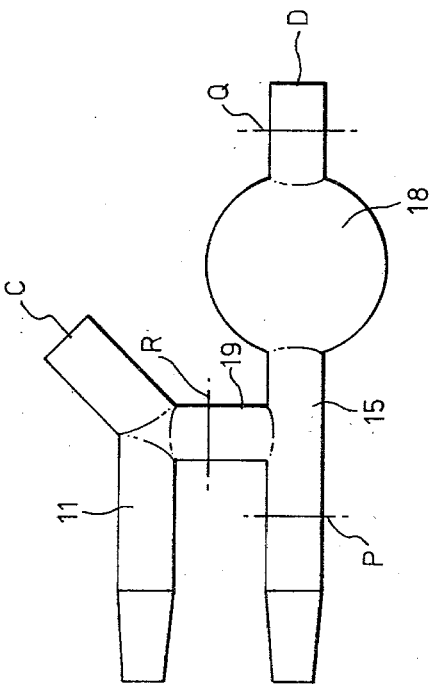
FIG. 4 shows yet another form of irrigation device.

In FIG. 4, another form of irrigation device is shown and similar parts like numbered to correspond with FIG. 1.

The irrigation device described can be formed as relatively compact units, especially the device described with reference to FIG. 3.

I claim:

1. A device for use in the irrigation of a body cavity comprises:
(a) a first passageway having a liquid inlet at one end thereof, which is connectible to a source of irrigation liquid and a liquid outlet at the other end thereof which is connected to or connectible to the inlet passageway of a dual flow flow catheter,
(b) a second passageway having a liquid inlet at one end thereof which is connected to or connectible to the outlet passageway of said dual flow catheter and a liquid outlet at the other end thereof,
(c) an enlarged deformable portion of the second passageway located downstream of said one end of the second passageway,
(d) first flow-controlling means downstream of the enlarged deformable portion to prevent or impede the flow of liquid through the second passageway,
the arrangement being such that when the flow-controlling means are operated to prevent or impede the flow of liquid through the second passageway and the enlarged deformable portion is manipulated to reduce its volume, the flow of liquid in the second passageway upstream of the enlarged deformable portion and in the outlet passageway of the dual flow catheter is reversed.

2. An irrigation device as claimed in claim 1 additionally comprising a by-pass passageway connecting the first and second passageways and a second flow-controlling means in said by-pass passageway to prevent or impede the flow of liquid through the by-pass passageway.

3. An irrigation device as claimed in claim 1 additionally comprising third flow-controlling means located between said one end of the second passageway and the enlarged deformable portion of the second passageway.

4. An irrigation device as claimed in claim 1 wherein the first and second passageways are formed integrally with the inlet and outlet passageways respectively of a dual flow catheter.

5. An irrigation device as claimed in claim 1 in which the enlarged deformable portion is substantially spherical.

6. An irrigation device as claimed in claim 1 in which the enlarged deformable portion is substantially cylindrical the cylinder having a larger diameter than the second passageway.

7. An irrigation device as claimed in claim 6 in which the first passageway passes through the substantially cylindrical enlarged deformable portion.

8. An irrigation device as claimed in claim 1 wherein the first flow-controlling means comprise a manually-operable clip.

9. An irrigation device as claimed in claim 2 wherein the second flow-controlling means comprise a manually-operable clip.

10. An irrigation device as claimed in claim 3 wherein the third flow-controlling means comprise a manually operable clip.

* * * * *